United States Patent
Zhang et al.

(10) Patent No.: US 9,186,273 B2
(45) Date of Patent: *Nov. 17, 2015

(54) METHODS OF TREATING PAINS ASSOCIATED WITH NEUROMA, NERVE ENTRAPMENT, AND OTHER CONDITIONS

(75) Inventors: Jie Zhang, Salt Lake City, UT (US); Robert Lippert, Park City, UT (US)

(73) Assignee: Nuvo Research Inc., Mississauga, Ontario (CA)

( * ) Notice: Subject to any disclaimer, the term of this patent is extended or adjusted under 35 U.S.C. 154(b) by 49 days.

This patent is subject to a terminal disclaimer.

(21) Appl. No.: 12/773,239

(22) Filed: May 4, 2010

(65) Prior Publication Data

US 2011/0112189 A1    May 12, 2011

Related U.S. Application Data

(60) Provisional application No. 61/175,181, filed on May 4, 2009.

(51) Int. Cl.
  *A61K 31/24*     (2006.01)
  *A61F 7/02*      (2006.01)
  *A61K 9/70*      (2006.01)
  *A61K 31/167*    (2006.01)
  *A61K 31/245*    (2006.01)
  *A61K 31/445*    (2006.01)
  *A61F 7/03*      (2006.01)
  *A61F 7/00*      (2006.01)

(52) U.S. Cl.
  CPC ............... *A61F 7/02* (2013.01); *A61K 9/7023* (2013.01); *A61K 31/167* (2013.01); *A61K 31/245* (2013.01); *A61K 31/445* (2013.01); *A61F 7/03* (2013.01); *A61F 7/034* (2013.01); *A61F 2007/0071* (2013.01); *A61F 2007/0261* (2013.01); *A61F 2007/0292* (2013.01)

(58) Field of Classification Search
  None
  See application file for complete search history.

(56) References Cited

U.S. PATENT DOCUMENTS

| | | |
|---|---|---|
| 3,929,131 A | 12/1975 | Hardwick |
| 4,210,670 A | 7/1980 | Cooke |
| 4,230,105 A | 10/1980 | Hardwood |
| 4,230,150 A | 10/1980 | Scaramucci |
| 4,286,592 A | 9/1981 | Chandrasekaran |
| 4,529,601 A | 7/1985 | Broberg et al. |
| 4,685,911 A | 8/1987 | Konno et al. |
| 4,693,706 A | 9/1987 | Ennis, III |
| 4,747,841 A | 5/1988 | Kuratomi et al. |
| 4,830,855 A | 5/1989 | Stewart |
| 4,879,119 A | 11/1989 | Konno et al. |
| 4,898,592 A | 2/1990 | Latzke et al. |
| 4,911,707 A | 3/1990 | Heiber et al. |
| 4,913,957 A | 4/1990 | Strack et al. |
| 4,963,360 A | 10/1990 | Argaud |
| 4,994,049 A | 2/1991 | Latzke et al. |
| 5,108,710 A | 4/1992 | Little et al. |
| 5,114,411 A | 5/1992 | Haber et al. |
| 5,128,137 A | 7/1992 | Muller et al. |
| 5,147,339 A | 9/1992 | Sundstrom |
| 5,213,129 A | 5/1993 | Someah et al. |
| 5,217,718 A | 6/1993 | Colley et al. |
| 5,229,133 A | 7/1993 | Wright et al. |
| 5,276,032 A | 1/1994 | King et al. |
| 5,279,594 A | 1/1994 | Jackson |
| 5,298,257 A | 3/1994 | Bannon et al. |
| 5,329,976 A | 7/1994 | Haber et al. |
| 5,330,452 A | 7/1994 | Zook |
| 5,364,350 A | 11/1994 | Dittmann |
| 5,378,730 A | 1/1995 | Lee et al. |
| 5,534,021 A | 7/1996 | Dvoretzky et al. |
| 5,580,573 A | 12/1996 | Kydonieus et al. |
| 5,626,571 A | 5/1997 | Young et al. |
| 5,651,768 A | 7/1997 | Sibalis |
| 5,658,583 A | 8/1997 | Zhang et al. |
| 5,662,624 A | 9/1997 | Sundstrom et al. |
| 5,679,373 A | 10/1997 | Wick et al. |
| 5,728,057 A | 3/1998 | Ouellette et al. |
| 5,728,058 A | 3/1998 | Ouellette et al. |
| 5,728,146 A | 3/1998 | Burkett et al. |
| 5,730,721 A | 3/1998 | Hyatt et al. |
| 5,733,255 A | 3/1998 | Dinh et al. |
| 5,735,889 A | 4/1998 | Burkett et al. |
| 5,741,318 A | 4/1998 | Ouellette et al. |

(Continued)

FOREIGN PATENT DOCUMENTS

| | | |
|---|---|---|
| CA | 2228137 | 2/1997 |
| CA | 2408585 | 2/1997 |

(Continued)

OTHER PUBLICATIONS

Argoff (Curr Pain and Headache Reports 6:375-378, 2002).*

(Continued)

*Primary Examiner* — Craig Ricci
(74) *Attorney, Agent, or Firm* — Thorpe North & Western LLP (57) ABSTRACT

The present disclosure is drawn to methods for treating various types of pain. Specifically, a method for treating various types of pain includes the application of an analgesic system to a skin surface of a subject experiencing the pain and maintaining the analgesic system on the skin surface for a period of time of at least 30 minutes. The analgesic system applied to the skin surface can include a heating component and a local anesthetic formulation which includes at least one local anesthetic. The heating component can be capable of heating the skin surface to a temperature of 36° C. to 42° C.

21 Claims, 1 Drawing Sheet

(56) References Cited

U.S. PATENT DOCUMENTS

| | | | |
|---|---|---|---|
| 5,776,952 A | 7/1998 | Liedtke | |
| 5,837,005 A | 11/1998 | Viltro et al. | |
| 5,840,755 A | 11/1998 | Liedtke | |
| 5,860,945 A | 1/1999 | Cramer et al. | |
| 5,904,710 A | 5/1999 | Davis et al. | |
| 5,906,637 A | 5/1999 | Davis et al. | |
| 5,906,830 A | 5/1999 | Farinas et al. | |
| 5,919,479 A | 7/1999 | Zhang | |
| 5,925,072 A | 7/1999 | Cramer et al. | |
| 5,980,562 A | 11/1999 | Ouellette et al. | |
| 5,984,995 A | 11/1999 | White | |
| 5,993,836 A | 11/1999 | Castillo | |
| 6,019,782 A | 2/2000 | Davis et al. | |
| 6,020,040 A | 2/2000 | Cramer et al. | |
| 6,024,761 A | 2/2000 | Barone et al. | |
| 6,042,673 A | 3/2000 | Johnson et al. | |
| 6,048,326 A | 4/2000 | Davis et al. | |
| 6,245,347 B1 | 6/2001 | Zhang | |
| 6,261,595 B1 | 7/2001 | Stanley et al. | |
| 6,284,266 B1 | 9/2001 | Zhang et al. | |
| 6,303,142 B1 | 10/2001 | Zhang et al. | |
| 6,306,431 B1 | 10/2001 | Zhang | |
| 6,340,472 B1 | 1/2002 | Zhang | |
| 6,453,648 B1 | 9/2002 | Zhang | |
| 6,465,006 B1 | 10/2002 | Zhang | |
| 6,465,709 B1 * | 10/2002 | Sun et al. | 602/48 |
| 6,488,959 B2 | 12/2002 | Stanley et al. | |
| 6,528,086 B2 | 3/2003 | Zhang | |
| 6,546,281 B1 | 4/2003 | Zhang | |
| 6,613,350 B1 | 9/2003 | Zhang et al. | |
| 6,726,673 B1 | 4/2004 | Zhang et al. | |
| 6,756,053 B2 | 6/2004 | Zhang et al. | |
| 6,756,426 B2 | 6/2004 | Brother et al. | |
| 6,780,426 B2 | 8/2004 | Zhang et al. | |
| 6,890,553 B1 | 5/2005 | Sun | |
| 6,929,131 B1 | 8/2005 | Landi | |
| 6,955,819 B2 | 10/2005 | Zhang et al. | |
| 7,718,674 B2 | 5/2010 | Aberg | |
| 2001/0037104 A1 | 11/2001 | Zhang et al. | |
| 2002/0119186 A1 | 8/2002 | Zhang et al. | |
| 2003/0012830 A1 | 1/2003 | Small | |
| 2003/0138505 A1 | 7/2003 | Fischer et al. | |
| 2005/0209319 A1 | 9/2005 | Cundy | |
| 2006/0078600 A1 | 4/2006 | Muller | |
| 2006/0147510 A1 | 7/2006 | Galer | |
| 2007/0059351 A1 | 3/2007 | Murrell et al. | |
| 2007/0068508 A1 * | 3/2007 | York-Leung Wong | 126/263.02 |
| 2007/0189978 A1 | 8/2007 | Zhang et al. | |
| 2007/0196323 A1 | 8/2007 | Zhang et al. | |
| 2007/0196458 A1 | 8/2007 | Zhang et al. | |
| 2008/0021051 A1 | 1/2008 | Wilson | |
| 2011/0015229 A1 | 1/2011 | Zhang et al. | |
| 2011/0086913 A1 | 4/2011 | Zhang | |

FOREIGN PATENT DOCUMENTS

| | | |
|---|---|---|
| EP | 0304227 | 2/1989 |
| EP | 2205496 | 4/2009 |
| EP | 2163956 | 3/2010 |
| GB | 2163956 | 3/1986 |
| GB | 2205496 | 12/1988 |
| JP | H05-170644 | 9/1993 |
| JP | H11-510075 A | 9/1999 |
| JP | 2002/525172 A | 8/2002 |
| JP | 2003/510259 A | 3/2003 |
| JP | 2009174243 | 8/2009 |
| WO | WO 85/02124 | 5/1985 |
| WO | WO 88/09169 | 12/1988 |
| WO | WO 93/07842 | 4/1993 |
| WO | WO 93/07870 | 4/1993 |
| WO | WO 97/01310 | 1/1997 |
| WO | WO 97/01311 | 1/1997 |
| WO | WO 97/01312 | 1/1997 |
| WO | WO 97/01313 | 1/1997 |
| WO | WO 97/04728 | 2/1997 |
| WO | WO 97/36968 | 10/1997 |
| WO | WO 97/49361 | 12/1997 |
| WO | WO 98/00118 | 1/1998 |
| WO | WO 98/28021 | 7/1998 |
| WO | WO 98/28024 | 7/1998 |
| WO | WO 98/29063 | 7/1998 |
| WO | WO 98/29064 | 7/1998 |
| WO | WO 98/29065 | 7/1998 |
| WO | WO 98/29066 | 7/1998 |
| WO | WO 98/29067 | 7/1998 |
| WO | WO 99/09917 | 3/1999 |
| WO | WO 99/09918 | 3/1999 |
| WO | WO 00/18339 | 4/2000 |
| WO | WO 01/22907 | 4/2001 |
| WO | WO 2007/070679 | 6/2007 |
| WO | WO 2008/106220 A1 | 9/2008 |
| WO | WO 2008/150995 | 12/2008 |
| WO | WO 2009/053572 | 4/2009 |
| WO | WO 2010/080831 | 7/2010 |
| WO | WO 2010/114973 | 10/2010 |
| WO | WO 2010/129542 | 11/2010 |
| WO | WO 2011/028542 | 3/2011 |

OTHER PUBLICATIONS

Ohzeki et al (Yakugaku Zasshi 128:611-616, 2008).*
Risovic et al (Lek Sirov vol. XX(No. 21):157-161, 2001.*
Yap (Ann Acad Med Singapore 36:43-48, 2007).*
Tadicherla et al (Therapeutics and Clin Risk Management 2:99-113, 2006).*
Nalamachu et al (MedGenMed 8:33, 2006).*
Burch (OsteoArthritis and Cartilage 12:253-255, 2004).*
Radnovich et al (Int J Gen Med 6:641-646, 2013).*
PCT Application PCT/US10/33538; filed May 4, 2010; Jie Zhang.
PCT Application PCT/US10/29580; filed Apr. 1, 2010; Jie Zhang.
PCT Application PCT/US10/46523; filed Aug. 24, 2010; Jie Zhang.
Moghtaderi et al.; EMLA Cream for Carpal Tunnel Syndrome: How it Compares with Steroid Injection; Electomyogr Clin Neurophysiol; Sep.-Oct. 2009; vol. 49 No. 6-7; pp. 287-289 (abstract only).
Nalamachu et al.; A Comparison of the Lidocaine Patch 5% vs Naproxen 500mg Twice Daily for the Relief of Pain Associated with Carpal Tunnel Syndrome: a 6-Week, Randomized, Parallel-Group Study; MedGenMed; Aug. 2006; vol. 8 No. 3.
Nalamachu et al.; Lidocaine Patch 5 for Carpal Tunnel Syndrome: How it Compares with Injections: a Pilot Study; J Fam Pract; Mar. 2006; vol. 55 No. 3; pp. 209-214.
Wallace et al.; Evaluation of the Depth and Duration of Anesthesia From Heated Lidocaine-Tetracaine (Synera) Patches Compared with Placebo Patches Applied to Healthy Adult Volunteers; Regional Anesthesia and Pain Medicine; Nov.-Dec. 2010; vol. 35, No. 6; pp. 507-513.
US Application PCT/US10/33538; filed Nov. 11, 2010; Jie Zhang; International Search Report issued Jul. 30, 2010.
Mack Publishing Company, "Stability of Pharmaceutical Products", Pharmaceutical Sciences, p. 1481-2,1985.
McCafferty et al., Comparative In Vivo and In Vitro Assessment of the Percutaneous Absorption of Local Anaesthetics:, Br. J. Anasth., vol. 60, 1988, p. 64-69.
Woolfson et al., "Concentration Response Analysis of Percutaneous Local Anesthetic Formulations", BR. J. Anaesth., vol. 61, 1988, p. 590-592.
McCafferty et al., "In Vivo Assessment of Percutaneous Local Anesthetic Preparations", Br. J. Anaesth., vol. 62, 1989, p. 18-21.
Knutson et al., "Solvent-Mediated Alterations of the Stratum Corneum", Journal of Controlled Release vol. 11, 1990, p. 93-103.
Lycka, "EMLA, a New and Effective Topical Anesthetic", J. Dermotol. Surg. Oncol., vol. 18,1992, p. 859-862.
McCafferty et al., "New Patch Delivery System for Percutaneous Local Anesthesia", Br. J. Anaesth., vol. 71, 1993, p. 370-374.
Sakamoto et al., "Dermal Patch Anesthesia: Comparison of 10% Lignocaine Gel with Absorption Promoter and EMLA Cream", Anesthesia, vol. 48, 1993, p. 390-392.

(56) References Cited

OTHER PUBLICATIONS

Woolfson, "Percutaneous Local Anesthesia", Formulation of Local Anesthsia for Percutaneous Delivery (Ch. 5), E. Horwood, NY, 1993 p. 166-170.
Astra USA, Inc., "Elma Cream (lidocaine 2.5% and prilocaine 2.5%)", Product Information Form for American Hospital Formulary Service, 1993, p. 1-28.
PCT Application PCT/US10/33538; filed May 4, 2010; ISR mailed Jul. 30, 2010.
PCT Application PCT/US10/29580; filed Apr. 1, 2010; ISR mailed Aug. 4, 2010.
PCT Application PCT/US10/20255; filed Jan. 6, 2010; ISR mailed Mar. 16, 2010.
U.S. Appl. No. 12/752,384, filed Apr. 1, 2010; Jie Zhang.
U.S. Appl. No. 12/652,502, filed Jan. 5, 2010; Jie Zhang; office action issued Nov. 17, 2011.
Croxtall, Lidocaine/tetracaine medicated plaster: in minor dermatological and needle puncture procedures. Drugs. 2010; 70:2113-2120.
Shainhouse, Topical anesthetics: physiology, formulations, and novel delivery systems. Am J. Drug Delivery. 2004; 2:89-99.
Shaikh, The influence of a eutectic mixture of lidocaine and prilocaine on minor surgical procedures: a randomized controlled double-blind trial. Dermatol Surg. 2009; 35:948-951.
Tang, Study on the efficacy of ELA-Max (4% liposomal lidocaine) compared with EMLA cream (eutectic mixture of local anesthetics) using thermosensory threshold analysis in adult volunteers. J Dermatol Treat. 2004; 15:84-87.
Sawyer, Heated lidocaine/tetracaine patch (Synera, Rapydan) compared with lidocaine/prilocaine cream (EMLA) for topical anaesthesia before vascular access. Br J Anaesth. 2009; 102:210-215.
Sethna, A randomized controlled trial to evaluate S-Caine patch for reducing pain associated with vascular access in children. Anesthesiology. 2005; 102:403-408.
Singer, Warm lidocaine/tetracaine patch versus placebo before pediatric intravenous cannulation; a randomized controlled trial. Ann Emerg Med. 2008; 52:41-47.
Berman, Self-warming lidocaine/tetracaine patch effectively and safely induces local anesthesia during minor dermatologic procedures. Dermatol Surg. 2005; 31:135-138.
Curry, Use of the Syneral patch for local anesthesia before vascular access procedures: a randomized, double-blind, placebo-controlled study. Pain Med. 2007;8:489-502.
Schecter, Randomized, double-blind, placebo-controlled study evaluating the lidocaine/tetracaine patch for induction of local anesthesia prior to minor dermatologic procedures in geriatric patients. Dermatol Surg. 2005; 31:287-291.
Mehra, Lidocaine toxicity. Anesth Prog. 1998; 45:38-41.
Peers, Patellar tendinopathy in atheletes: current diagnostic and therapeutic recommendations. Sports Medicine. 2005; 35:71-87.
Rees, Current concepts in the management of tendon disorders. Rheumatology (Oxford). 2006; 45:508-521.
Abate, Pathogenesis of tendinopathies: inflammation or degeneration? Arthritis Research and Therapy. 2009; 11:235.
McCarty, Results of controlled study of combination therapy with azathioprine and methotrexate in the treatment of rheumatoid arthritis revisited: comment on the article by Willkens et al. Arthritis Rheum. 1996; 39:1436-1437.
Lian, Pronociceptive and antinociceptive neuromediators in patellar tendinopathy. Am J Sports Med. 2006; 34:1801-1808.
Forsgren, Vascular NK-1 receptor occurrence in normal and chronic painful Achilles and patellar tendons: studies on chemically unfixed as well as fixed specimens. Regul Pept. 2005; 126:173-181.
Jessell, Opiate analgesics inhibit substance P release from rat trigeminal nucleus. Nature. 1977; 268:549-551.
Alfredson, In vivo microdialysis and immunohistochemical analyses of tendon tissue demonstrated high amounts of free glutamate and glutamate NMDAR1 receptors, but no signs of inflammation, in Jumper's knee. J. Orthop Res. 2001; 19:881-886.
Alfredson, Chronic tendon paid: no signs of chemical inflammation but high concentrations of the neurotransmitter glutamate. Implications for treatment? Curr Drug Targets. 2002; 3:43-54.
Scott, VGluT2 expression in painful Achilles and patellar tendinosis: evidence of local glutamate release by tenocytes. J Orthop Res. 2008; 26:685-692.
Magra, VOCCs and TREK-1 ion channel expression in human tenocytes. Am J Physiol Cell Physiol. 2007; 292:C1053-C1060.
Ritchie, On the mode of action of local anesthetics. Annual Review of Pharmacology. 1966; 6:405-430.
Sugimoto, Local anaesthetics have different mechanisms and sites of action at the recombinant N-methyl-D-aspartate (NMDA) receptors. British Journal of Pharmacology. 2003; 138:876-882.
Tadicherla, Percutaneous dermal drug delivery for local pain control. Therapeutics and Clinical Risk Management. 2006; 2:99-113.
Visentini, The VISA score: an index of severity of symptoms in patients with jumper's knee (patellar tendinosis). Victorian Institute of Sport Tendon Study Group. Journal of Science and Medicine in Sport. 1998; 1:22-28.
Nishizawa, The inhibition of the N-methyl-D-aspartate receptor channel by local anesthetics in mouse CA1 pyramidal neurons. Anesth Analg. 2002; 94:325-30, table.
Frohm, Patellar tendinopathy—on evaluation methods and rehabilitation techniques. Stockholm: Karolinska University Press; 2006.
Khan, The painful nonruptured tendon: clinical aspects. Clin Sports Med. 2003; 22:711-725.
Khan, Patellar tendinosis (jumper's knee): findings at histopathologic examination, US, and MR imaging. Victorian Institute of Sport Tendon Study Group. Radiology. 1996; 200:821-827.
Astrom, No effect of piroxicam on achilles tendinopathy. A randomized study of 70 patients. Acta Orthop Scand. 1992; 63:631-634.
Khan, Overuse tendon injuries: where does the pain come from? Sports Medicine and Arthroscopy Review. 2000; 8:17-31.
Riley, Tendinopathy—from basic science to treatment. Nature Clinical Practice Rheumatology. 2008; 4:82-89.
Scott, VEGF expression in patellar tendinopathy: a preliminary study. Clin Orthop. 2008; 466:1598-1604.
Astrom, Chronic Achilles tendinopathy. A survey of surgical and histopathologic findings. Clin Orthop. 1995; 151-164.
Danielson, Studies on the importance of sympathetic innervation, adrenergic receptors, and a possible local catecholamine production in the development of patellar tendinopathy (tendinosis) in man. Microscopy Research and Technique. 2007; 70:310-324.
Jensen, Evaluation of eccentric exercise in treatment of patellar tendinitis. Physical Therapy. 1989; 69:211-216.
Cannell, A randomised clinical trial of the efficacy of drop squats or leg extension/leg curl exercises to treat clinically diagnosed jumper's knee in athletes: pilot study. Br J Sports Med. 2001; 35:60-64.
Centini, Suicide due to oral ingestion of lidocaine: a case report and review of the literature. Forensic Science International. 2007; 171:57-62.
Cada et al; Lidocaine/Tetracaine Patch; Hospital Pharmacy; 2006; pp. 265-273; vol. 41, No. 3.
Young et al.; What's New in Topical Anesthesia; Clinical Pediatric Emergency Medicine; Dec. 3, 2007; pp. 232-239; vol. 8, No. 4.
Hines et al; Use of Lidocaine Patch 5% for Chronic Low Back Pain: A Report of Four Cases; Pain Medicine; Dec. 2002; pp. 361-365; American Academy of Pain Medicine.

* cited by examiner

METHODS OF TREATING PAINS ASSOCIATED WITH NEUROMA, NERVE ENTRAPMENT, AND OTHER CONDITIONS

This application claims the benefit of U.S. Provisional Patent Application No. 61/175,181, filed May 4, 2009, which is incorporated herein by reference in its entirety.

BACKGROUND OF THE INVENTION

Pains associated with nerve conditions such as nerve entrapment and neuroma are suffered by many people. Examples of these pains and similar pains include point pain, nerve entrapment pain (carpal tunnel syndrome, ulnar neuropathy, pudendal nerve entrapment), focal pain, IT band pain, pain associated with trigger points, occipital neuralgia, headaches associated with trigger point pain, pain associated with arthritis, pain associated with injury, and from over use of muscles or joints.

These pains are frequently treated with opioid and non-opioid analgesics delivered orally or by injection. Unfortunately, these treatment options suffer from various drawbacks and undesirable side-effects. These undesirable side-effects are frequently due to their systemic delivery. Accordingly, research continues into alternative methods of ameliorating these pains.

DETAILED DESCRIPTION

Before particular embodiments of the present invention are disclosed and described, it is to be understood that this invention is not limited to the particular process and materials disclosed herein as such may vary to some degree. It is also to be understood that the terminology used herein is used for the purpose of describing particular embodiments only and is not intended to be limiting, as the scope of the present invention will be defined only by the appended claims and equivalents thereof.

In describing and claiming the present invention, the following terminology will be used.

The singular forms "a," "an," and "the" include plural referents unless the context clearly dictates otherwise. Thus, for example, reference to "a local anesthetic" includes reference to one or more of such compositions.

"Skin" is defined to include human skin (intact, diseased, ulcerous, or broken), and mucosal surfaces that are usually at least partially exposed to air such as lips, genital and anal mucosa, and nasal and oral mucosa.

It is also noted that "local anesthetics" in appropriate formulations can be used to provide skin "anesthesia," which by medical definition means preventing a pain before it happens, such as preventing a pain caused by needle stick. The present disclosure, however, is related to methods of using a local anesthetic formulation to provide "analgesia," which by medical definition means to reduce or eliminate an existing pain, e.g., nerve entrapment pain; neuroma pain; headache associated with neuralgia, such as occipital neuralgia or trigeminal neuralgia; connective tissue pain such as iliotibial band pain, blood vessel pain, tendinopathy pain, medial tibial stress syndrome pain, bursitis, etc.; arthritis pain such as osteoarthritis pain or rheumatoid arthritis pain; pain associated with injury such as fracture, severance, break, sprain, strain, tear, point pain (e.g., trigger point pain or hit point pain), focal pain, or bruise; or combinations of these pains.

The terms "controlled heating" and "controlled heat" are defined as heat application that is capable of heating a skin surface to pre-determined narrow temperature range for a predetermined duration. A controlled heating device that can be used in accordance with systems and methods of the present disclosure can be configured to generate heat promptly when activated. Controlled heating can be achieved through special design of the heating component. For example, controlled heating can be achieved through the use of a properly configured heating element(s) including an exothermic chemical composition. Considerations in generating controlled heat with an exothermic heating component include proper ratios and exothermic chemical compositions used, as well as physical constraints put on the exothermic chemical compositions, e.g., limiting air flow or oxygen contact, spatial configuration of individual heating elements, conductivity of materials used with the exothermic chemical composition, etc. In one embodiment, the heating component can provide heat at a temperature greater than body temperature, but less than a temperature that would cause irreversible skin damage, e.g., burn the skin. An exemplary temperature range that can be implemented for use can be from about 35° C. to about 47° C. In one embodiment, another temperature range can be from about 36° C. to 42° C. Other desired temperature ranges include from about 38° C. to 42° C. or from 36° C. to 40° C.

"Nerve entrapment" pain in the present disclosure is the same as that commonly used in modern medicine. This type of pain relates to nerves that are under compression or pressure, or are otherwise constricted. Often these ailments are a result of chronic compression of the nerve(s). Such pains include but are not limited to pains associated with carpal tunnel syndrome, ulnar neuropathy, pudendal nerve entrapment, cubital tunnel syndrome, Guyon canal syndrome, posterior interosseous nerve syndrome, supracapular nerve entrapment, lateral femoral cutaneous nerve entrapment, and Tarsal tunnel syndrome.

When referring to pain associated with "neuroma" in the present disclosure, this includes pains associated with neoplastic tumors or nerve injuries, including traumatic neuroma (often as a result of surgery) and Morton's neuroma (a mononeuropathy of the foot).

Headache or pain associated with "occipital neuralgia" in the present disclosure has the same meaning as that defined in modern medicine. Occipital neuralgia causes a distinct type of headache often accompanied by piercing, throbbing, or electric-shock-like chronic pain in the upper neck, back of the head, and behind the ears, usually on one side of the head. Occasionally, pain is experienced in the scalp, forehead, and behind the eyes. The pain is associated with the greater and lesser occipital nerves, from the upper spinal column to the neck, and scalp at the back of the head. The pain can be caused by irritation or injury to the nerves, which can be the result of trauma to the back of the head, pinching of the nerves by overly tight neck muscles, compression of the nerve as it leaves the spine due to osteoarthritis, or tumors or other types of lesions in the neck. Other causes and symptoms are also possible.

The term "connective tissue" as used herein generally refers to connective tissue proper, excluding bone, cartilage and blood. Connective tissue can be areolar (or loose) connective tissue, adipose connective tissue, fibrous (or dense) connective tissue, elastic connective tissue, and reticular connective tissue. Specific examples of connective tissue herein include tendons, ligaments, iliotibial band, blood vessels, etc.

The phrase "iliotibial band pain" in the present disclosure means the pain associated with the Iliotibial syndrome. Inflammation of the iliotibial band, which is a thick band of fibrous tissue that runs down the outside of the leg, causes the pain.

Pain associated "over use" of joints in the present disclosure includes, but is not limited to, bursitis; tendinopathy including tendonosis, tendonitis or "tennis elbow," patellar tendonitis, clavicular tendonitis, medial tibial stress syndrome, focal pain, point pain (e.g., trigger point pain or hit point pain), etc.

Pain associated "damage" or "injury" of joints in the present disclosure includes, but is not limited to, tissue sprains, fractures, tears, and bruises, e.g., hamstring injuries, sprained ankle, hip pointer bruise, etc.

Pain associated with "arthritis" in the present disclosure relates to pain associated with arthritis, including osteoarthritis and rheumatoid arthritis.

As used herein, the term "about" is used to provide flexibility to a numerical range endpoint by providing that a given value may be "a little above" or "a little below" the endpoint. The degree of flexibility of this term can be dictated by the particular variable and would be within the knowledge of those skilled in the art to determine based on experience and the associated description herein.

As used herein, a plurality of local anesthetics, compounds, and/or heating mechanisms may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 0.01 to 2.0 mm" should be interpreted to include not only the explicitly recited values of about 0.01 mm to about 2.0 mm, but also include individual values and sub-ranges within the indicated range. Thus, included in this numerical range are individual values such as 0.5, 0.7, and 1.5, and sub-ranges such as from 0.5 to 1.7, 0.7 to 1.5, and from 1.0 to 1.5, etc. Furthermore, such an interpretation should apply regardless of the breadth of the range or the characteristics being described. Additionally, it is noted that all percentages are in weight, unless specified otherwise.

With this background in mind, the present disclosure is drawn to methods for treating nerve entrapment pain; neuroma pain; headache associated with neuralgia, such as occipital neuralgia or trigeminal neuralgia; connective tissue pain such as iliotibial band pain, blood vessel pain, tendinopathy pain, medial tibial stress syndrome pain, bursitis, etc.; arthritis pain such as osteoarthritis pain or rheumatoid arthritis pain; pain associated with injury such as fracture, severance, break, sprain, strain, tear, focal pain from injury, point pain from injury (e.g., trigger point pain or hit point pain), or bruise; or combinations of these pains. Specifically, a method for treating the aforementioned pains includes the application of an analgesic system to a skin surface of a subject experiencing the pain and maintaining the analgesic system on the skin surface for a period of time of at least 30 minutes. The application site can typically be a skin area over the pain, and can be over one or more trigger points. The analgesic system applied to the skin surface can include a heating component and a local anesthetic formulation including at least one local anesthetic. The heating component can be capable of heating the skin surface to a temperature of 36° C. to 42° C. for a sustained period of time within this narrow temperature range.

The methods of the present disclosure can harness the benefits of both increased delivery of the local anesthetic and the therapeutic effect of heating. Furthermore, in some embodiments, the use of heat can actually improve the penetration and benefit of the local anesthetic(s) compared to the use of the same formulation without application of heat. Stated another way, the methods of the present application can provide enhanced transdermal delivery of the local anesthetic through the use of controlled heating, and the added benefit provided by the heat itself. As the skin is heated, the permeability of the skin to the local anesthetics drugs can increase. Additionally, the heating of the skin itself is also believed to reduce the existing pain. Accordingly, the combination of the transdermal delivery of the local anesthetic from the local anesthetic formulation with the heat from the heating component can cause a more efficient, i.e. faster and more effective, reduction in pain than either the drug or the heat alone.

As described above, the analgesic systems used in the methods of the present disclosure can comprise two major components: a controlled heating component and a local anesthetic formulation. The local anesthetic formulation can be incorporated in a patch and can include an amount of the local anesthetic to provide, with the help of the heating component, sufficient transdermal delivery of the local anesthetic for reducing or eliminating existing pain. A sufficient transdermal delivery of the local anesthetic is defined as a rate of delivery that is high enough to reduce the pain intensity (as measured by patient report of pain intensity) in an average patient by at least 20%, and often at least 30% or even 50%. With some patients and some conditions, complete pain relief can be achieved. The heating device can be configured for application over the patch and the human skin site. Additionally, the heating device can be configured to heat a skin site to which it is applied to a temperature that provides a therapeutic effect, such as from about 36° C. to about 42° C. The heating device can further be capable of maintaining the skin within the above temperature range for a period of time of at least 30 minutes, or in other embodiments, at least 1 hour.

As stated, the analgesic systems of the present disclosure can include a local anesthetic formulation and a heating component. The local anesthetic formulation can be designed to transdermally deliver at least one local anesthetic. The local anesthetic can generally be any local anesthetic known in the art. In one embodiment, the local anesthetic can be selected from the group consisting of tetracaine, lidocaine, prilocaine, ropivacaine, bupivacaine, benzocaine, and combinations thereof. In another embodiment, the local anesthetic formulation can include lidocaine base. In another embodiment, the local anesthetic formulation can include tetracaine base. In yet a further embodiment, the local anesthetic formulation can include a eutectic mixture of lidocaine base and tetracaine base. In another embodiment, the local anesthetic formulation can comprise at least 30 wt % (alone or in combination) of total local anesthetic, e.g., at least 30 wt % of a 1:1 (by weight) of a eutectic mixture of lidocaine and tetracaine (in combination), or at least 30 wt % of lidocaine or other local anesthetic base (alone). In still other embodiments, lower concentrations of local anesthetics can be used, e.g., at least 15 wt % local anesthetic, at least 20 wt % local anesthetic, or at least 25 wt % local anesthetic. For example, if using lidocaine alone, depending on the other formulation ingredients, 20 wt % of lidocaine alone may provide a similar effectiveness as a formulation with 30 wt % of lidocaine alone. Thus, the weight percentage guidelines described herein may be modified in order to achieve a desired therapeutic effect.

The local anesthetic formulation may also include other ingredients and excipients such as polymers, emulsifiers, chemical permeation enhancers, water or other solvents, and preservatives. In one embodiment, the local anesthetic formulation can include a solidification polymer such as polyvinyl alcohol. In another embodiment, the local anesthetic formulation can include an adhesive polymer which can be capable of adhering to skin.

The local anesthetic formulation portion of the analgesic system can have a skin contact region where the local anesthetic formulation contacts the skin surface. The size of the skin contact area can vary depending on the targeted region of the subject's body and the nature of the pain being treated. For example, in certain embodiments, the skin contact region can have an area of 2 $cm^2$ to 200 $cm^2$, 7 $cm^2$ to 150 $cm^2$, or 8 $cm^2$ to 15 $cm^2$. In various other embodiments, other size ranges may be appropriate. For example, the skin contact region can have an area of 3 $cm^2$ to 150 $cm^2$, 5 $cm^2$ to 130 $cm^2$, 6 $cm^2$ to 100 $cm^2$, 7 $cm^2$ to 80 $cm^2$, 8 $cm^2$ to 40 $cm^2$, or 8 to about 13 $cm^2$, etc. In one aspect of the disclosure, a layer of adhesive can be coated onto the analgesic outside the contact area, and/or between the skin and the local anesthetic formulation for affixing the system on the skin.

The heating components of the analgesic systems used in the method of the present application can be configured to raise the temperature of a skin surface to which the analgesic system is applied to a therapeutically effective temperature (for providing heat to the site and/or for providing enhanced drug delivery), e.g., about 36° C. to about 42° C. The heating component can further be configured to maintain the temperature of the skin surface in the above range for a period of time of at least 30 minutes. In one embodiment, the heating component can be configured to maintain the skin surface in the above described temperature range for a period of at least 60 minutes. In still other embodiments, the heating component can be configured to maintain the skin surface in the above described temperature range for a period of at least 2 hours, 4 hours, 6 hours, 8 hours, or 12 hours.

It is noted that regardless of the duration of heating, the analgesic systems used in the methods of the present disclosure can be configured to relieve nerve entrapment pain; neuroma pain; headache associated with neuralgia, such as occipital neuralgia or trigeminal neuralgia; connective tissue pain such as iliotibial band pain, blood vessel pain, tendinopathy pain (tendonosis and/or tendinitis), medial tibial stress syndrome pain, bursitis, etc.; arthritis pain such as osteoarthritis pain or rheumatoid arthritis pain; pain associated with injury such as from tissue fracture, severance, break, sprain, strain, tear, point pain from injury (e.g., trigger point or hit point pain), focal pain from injury, or bruise; or combinations of these pains. These pains can be relieved for a period of time beyond the period of time in which the heating component heats and/or which the analgesic system is maintained on the skin surface. In one embodiment, the methods of the present disclosure can provide relief of existing pain for a period of time of at least 4 hours. In another embodiment, the relief of pain can be for a period of time of at least 6 hours. In another embodiment, the relief of pain can be for a period of time of at least 12 hours.

In yet another embodiment, the system can be used on a chronic basis (at least once a day for at least 75% of the days in a period of time lasting at least two weeks). In a further embodiment, the system can be used more than once a day. The devices of the present disclosure can also be used for acute pain.

The heating components of the analgesic systems used in the methods of the present disclosure can generate heat through a number of mechanisms or means. In one embodiment, the heating component can generate the heat through chemical-based exothermic reactions. Other heating mechanisms can also be used, such as heating by phase transition of supersaturated solutions (such as phase transition of sodium acetate solutions), radiation (microwave or infrared, for example), electricity-resistor, combinations thereof, and/or other heating sources. In one embodiment, the heating component can be an electric heating device. Such electric heating device can be powered by a variety of sources, for example, battery and/or alternating electric current. Electric devices can be configured to provide a predetermined heating profile so that the heating profile is met automatically after engaging or turning on the electric device, e.g., use of timers, programmed electricity supply, finite batter power, etc. Alternatively, the heating profile can be met merely by providing heat at an appropriate temperature with an instruction to the user to remove the heating device after a specific period of time.

In one embodiment, the heating component can generate heat by an exothermic oxidative chemical reaction. The chemical-based exothermic oxidation reaction can generate heat through the contact of the oxidative material, e.g. iron, with ambient air. U.S. Pat. No. 6,756,053, which is incorporated herein by reference in its entirety, describes examples of exothermic heating components and devices.

The amount of exothermic chemical composition in the heating component can vary from depending on the desired duration of heating and the size of the heating component. It can be beneficial to limit the amount of the exothermic chemical composition in the heating component, as a large amount of exothermic chemical composition can cause the heating component to be excessively large or cumbersome and impractical for use. In one aspect, the heating device can include up to 2 grams of an exothermic chemical composition and can be configured to heat an area of skin greater than about 8 $cm^2$.

In addition to the oxidizable component, the exothermic heating composition can further include activated carbon, salt (such as sodium chloride), and water. In one aspect, a water-retaining substance, such as vermiculite or wood powder, can also be included in the heating component.

Depending on the configuration of the heating device, when stored for extended period of time the exothermic heating components can generate gas (believed to be methane and hydrogen) which can cause the packaging, in which the exothermic heating component is present, to puff up which can cause complications and problems with respect to storage and transportation. It has been discovered that the inclusion of certain amounts of sulfur-containing compounds, or salts thereof, such as elemental sulfur, sulfates, sulfites, sulfides, or thiosulfates, can reduce or eliminate this gas generation problem when included in the packaging.

Water content in the exothermic chemical composition can have an impact on the heating temperature profile of the heating device. The weight ratio of water to the rest of the ingredients in the exothermic heating component can be in the range of about 1:2.6 to about 1:5.0.

In one aspect, the exothermic chemical composition of the heating component can be manufactured in a manner so as to only have access to ambient oxygen through the holes in a cover that is made of air-impermeable material. In this way, the flow rate of oxygen from ambient air into the exothermic chemical composition, which in turn is a factor which can affect the amount and rate of heat generated by the heating component and the temperature of the skin surface on which the analgesic system is applied. Other factors which can influence the temperature and heat generation of the heating component can be the size of the heating component, the amount of the exothermic chemical composition in the heating component, the number and configuration of holes in the heating component's air impermeable cover material, etc.

Figure 1:
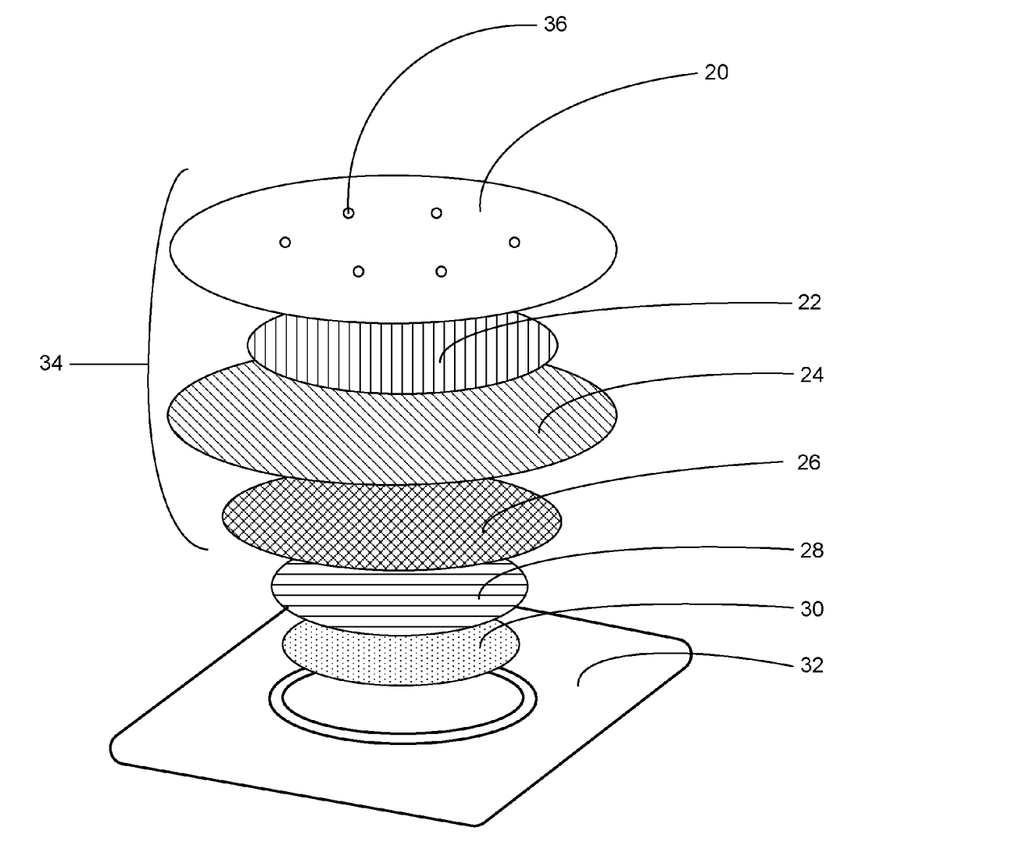
FIG. 1 is a schematic representation of an exemplary analgesic system in the form of a patch which can be used for treating various types of pain.

By way of example, FIG. 1 is a schematic profile of one embodiment of an analgesic system which could be used in accordance with the methods of the present application. The analgesic system includes a heating component 34 and a local anesthetic formulation 30. The heating component includes an air-impermeable top cover film 20 having a plurality of holes 36 therein. When exposed to ambient air, the holes allow for the passage of the ambient air through the air-impermeable top cover film to the exothermic chemical composition 22. The layer of exothermic chemical composition is disposed between the air-impermeable top cover film and an adhesive film layer 24. The adhesive film layer extends beyond the circumference of the exothermic chemical composition layer and the local anesthetic formulation layer and can function, at least in part, to adhere to the analgesic system to a skin surface. A heat sealable film layer 26 is below to the adhesive film layer and acts to impede the transfer of substances, particularly moisture, between the local anesthetic formulation layer and the exothermic chemical composition layer. Below the heat sealable film layer, a sodium-borate coated non-woven film layer 28 acts aids in gelling the local anesthetic formulation during manufacturing. The entire analgesic system is adhered in an air and moisture impermeable packing tray 32 which holds the local anesthetic formulation during storage.

EXAMPLES

The following examples illustrate the embodiments of the disclosure that are presently best known. However, it is to be understood that the following are only exemplary or illustrative of the application of the principles of the present disclosure. Numerous modifications and alternative compositions, methods, and systems may be devised by those skilled in the art without departing from the spirit and scope of the present disclosure. The appended claims are intended to cover such modifications and arrangements. Thus, while the present disclosure has been described above with particularity, the following examples provide further detail in connection with what are presently deemed to be the most practical and preferred embodiments of the disclosure.

Example 1

System for Treating Pain

The analgesic system described herein has two components: a drug component (drug formulation composition in a patch) and a heating component. Table 1 lists exemplary ingredients in the drug formulation. Table 2 lists exemplary ingredients of the heat generating medium. The drug formulation of the system has a skin contact area of about 10 $cm^2$.

TABLE 1

| Ingredient | Weight percentage (%) | Amount per patch | Function |
| --- | --- | --- | --- |
| Lidocaine base | 20.00 | 70.00 mg | Active ingredient |
| Tetracaine base | 20.00 | 70.00 mg | Active ingredient |
| Polyvinyl alchol (PVA) | 7.20 | 25.20 mg | Polymeric matrix |
| Sorbitan monopalmitate (Span 40) | 3.00 | 10.50 mg | Emulsifying agent |
| Purified Water | 49.68 | 173.88 mg | Solvent |
| Methyl parahydroxybenzoate | 0.10 | 0.35 mg | Preservative |
| Propylparagydroxybenzoate | 0.02 | 0.07 mg | Preservative |
| Sodium-borate coated nonwoven film | — | 10.84 $cm^2$ | Gelling of drug formulation |

TABLE 2

| COMPONENT | Weight Percentage (%) | Weight Per Patch (grams) |
| --- | --- | --- |
| Iron Powder Activated Carbon | 50 | 0.80 |
| Activated Carbon | 15.63 | 0.25 |
| Sodium Chloride | 6.25 | 0.10 |
| Wood Flour | 9.38 | 0.15 |
| Water | 18.74 | 0.3 |

The physical configurations of the drug component and the heating component, and their integration, are schematically shown in FIG. 1. The heat generating medium is enclosed in a closed space as shown in FIG. 1, and has access to the external environment only through the 6 holes on the air-impermeable cover. The diameter of each of the holes is about 1/16 of an inch. This heat generating medium can provide controlled heat at from 36 to 42° C. for a sustained period of time.

Example 2

System for Treating Pain

Four small analgesic systems described in Example 1 are prepared, except that the size of the patches are varied to have a skin contact area of 2 $cm^2$, 3 $cm^2$, 6 $cm^2$, and 8 $cm^2$, respectively. Thus, the weight percentages are the same for both the drug formulation (Table 1) and the heat generating medium (Table 2), but since the patches are smaller in size, the total amount of each ingredient is proportionally reduced. The number of holes or the size of the holes is also modified so that the total hole area (number of holes times the surface area of each hole) is adjusted proportionally in order to achieve a similar heating profile for the patch size, e.g., 1-6 holes of similar or slightly different size.

Example 3

System for Treating Pain

Four large analgesic systems described in Example 1 are prepared, except that the size of the patches are varied to have a skin contact area of 40 cm$^2$, 60 cm$^2$, 120 cm$^2$, 180 cm$^2$, respectively. Thus, the weight percentages are the same for both the drug formulation (Table 1) and the heat generating medium (Table 2), but since the patches are much larger in size, the total amount of each ingredient is proportionally increased. The number of holes or the size of the holes is also adjusted proportionally in order to achieve a similar heating profile for the patch size. The number of holes or the size of the holes is also modified so that the total hole area (number of holes times the surface area of each hole) is adjusted proportionally in order to achieve a similar heating profile for the patch size, e.g., 12-100 holes of similar or slightly different size.

Example 4

System for Treating Pain

An analgesic systems described in Example 1 is prepared, except that 40 wt % lidocaine base is used rather than 40 wt % of eutectic mixture of lidocaine and tetracaine base. Also, the patch size is modified to be 120 cm$^2$. Thus, the weight percentages are the same for both the drug formulation (Table 1) and the heat generating medium (Table 2), but since the patch is larger in size, the total amount of each ingredient is proportionally increased. The number of holes or the size of the holes is also modified so that the total hole area (number of holes times the surface area of each hole) is adjusted proportionally in order to achieve a similar heating profile for the patch size, e.g., 40-80 holes of similar or slightly different size.

Example 5

System for Treating Pain

An analgesic systems described in Example 1 is prepared, except that 40 wt % ropivacaine base is used rather than 40 wt % of eutectic mixture of lidocaine and tetracaine base. Also, the patch size is modified to be 120 cm$^2$. Thus, the weight percentages are the same for both the drug formulation (Table 1) and the heat generating medium (Table 2), but since the patch is larger in size, the total amount of each ingredient is proportionally increased. The number of holes or the size of the holes is modified so that the total hole area (number of holes times the surface area of each hole) is adjusted proportionally in order to achieve a similar heating profile for the patch size, e.g., 40-80 holes of similar or slightly different size.

Example 6

System for Treating Pain

An analgesic systems described in Example 1 is prepared, except that the heat generating medium is from an electric heating device, and the patch size is modified to 120 cm$^2$. Thus, the weight percentage is the same for the drug formulation (Table 1), but since the patch is larger in size, the total amount of each ingredient is proportionally increased.

Example 7

Treating Headache-Occipital Neuralgia

A patient is suffering from severe headache and is diagnosed as occipital neuralgia. After taking multiple oral medications, including opioids, to control the headache pain, an analgesic system similar to that described in Example 1 is applied to the neck twice daily, which reduces the pain and enables her to discontinue the oral pain medications.

Example 8

Treating Neuroma

A patient with ACL tear and knee arthroscopy surgery experiencing pain due to surgically induced neuroma is treated with an analgesic system similar to that in Example 1. The analgesic system is applied to either side of the knee (2 total patches). Pain relief is obtained 30 minute following the application and lasted 10-12 hours.

Example 9

Treating Nerve Entrapment

A patient with carpal tunnel syndrome experiencing pain is treated with an analgesic system similar to that in Example 1. The analgesic system is applied to the wrist of the patient. Pain relief is obtained 30 minute following the application and lasted 10-12 hours.

Example 10

Treating Focal Foot Pain

A patient is suffering focal foot pain due to repetitive use as a ballerina. A system similar to that in Example 1 is applied on the skin over the pain area. Pain relief is achieved following 30-minute application and lasts over eight hours. This analgesic system can be preferred over other topical treatments because it can be removed after 30 minutes and have continuous pain relief for a period of hours. This is useful when the patient prefers not to have an "unsightly" patch showing on the foot.

Example 11

Analgesic System and its Use to Treat Foot Pain

A patient suffering from reflex sympathetic dystrophy chronic pain on the foot after foot surgery takes medications included occasional opioids, oral NSAIDS, gabapentin, and others to control the pain. Three patches such as those described in Example 1 are applied sequentially to the site over 4 days, each left on the skin between 9 and 14 hours, provides near complete to complete pain relief in 25 minutes. The patient can discontinue all oral pain medications.

Example 12

Treating Severe Occipital Neuralgia

A patient is suffering from headaches and is diagnosed with severe occipital neuralgia. Two analgesic systems similar to that described in Example 3 (40 cm$^2$) are applied to the skin over the neck muscles twice daily, which reduces the pain and enables her to discontinue the oral pain medications. Alternatively, the analgesic systems are applied to each of the patient's temple twice daily. Combinations of placement locations can also be practiced to achieve maximum pain relief.

Example 13

Treating Connective Tissue Pain

A patient is suffering from connective tissue pain in his shoulder. An analgesic system similar to that described in Example 1 is applied to the shoulder area twice daily, which reduces the pain.

Example 14

Treating Osteoarthritis Arthritis Pain

A patient is suffering from pain associated with osteoarthritis in both of his knees. An analgesic system similar to that described in Example 3 (120 cm$^2$) is applied to each of the knee for two hours twice daily (every 12 hours), which reduces the pain significantly.

Example 15

Treating Rheumatoid Arthritis Pain

A patient is suffering from pain associated with rheumatoid arthritis in both of his knees. An analgesic system similar to that described in Example 3 (120 cm$^2$) is applied to each of the knee for one hour twice daily (every 12 hours), which reduces the pain significantly.

Example 16

Treating Pain Associated with Sprained Ankle

A basketball player sprains his ankle during playing basketball and is suffering from the pain associated with the injury. An analgesic system similar to that described in Example 3 (40 cm$^2$) is applied to ankle for one hour twice daily (every 12 hours), which reduces the pain significantly.

Example 17

Treating Pain Associated with Fractured Bone

A football player slightly fractures his collar bone during practice and is suffering from the pain associated with the injury. An analgesic system similar to that described in Example 3 (60 cm$^2$) is applied to skin area over the fracture for one hour twice daily (every 12 hours), which reduces the pain significantly.

Example 18

Treating Pain Associated with Dislocated Joint

A football player dislocates his right shoulder joint during practice. The dislocation was treated by a doctor but the patient is still suffering from the pain associated with the injury. An analgesic system similar to that described in Example 3 (120 cm$^2$) is applied to shoulder area for one hour twice daily (every 12 hours), which reduces the pain significantly.

Example 19

Treating Pain Associated with Dislocated Joint

A sprinter injures his hamstring tendon during practice and is suffering from the pain associated with injury. An analgesic system similar to that described in Example 3 (180 cm$^2$) is applied to skin area over the pain for two hour once daily (every 12 hours), which reduces the pain significantly.

Example 20

Treating Osteoarthritis Arthritis Pain

A patient is suffering from pain associated with osteoarthritis in both of his knees. An analgesic system similar to that described in Example 4 (120 cm$^2$) is applied to each knee for two hours twice daily (every 12 hours), which reduces the pain significantly.

Example 21

Treating Osteoarthritis Arthritis Pain

A patient is suffering from pain associated with osteoarthritis in both of his knees. An analgesic system similar to that described in Example 5 (120 cm$^2$) is applied to each knee for two hours twice daily (every 12 hours), which reduces the pain significantly.

Example 22

Treating Osteoarthritis Arthritis Pain

A patient is suffering from pain associated with osteoarthritis in both of his knees. An analgesic system similar to that described in Example 6 (120 cm$^2$) is applied to each knee for two hours twice daily (every 12 hours), which reduces the pain significantly.

Example 23

Treating Nerve Entrapment

A patient with carpal tunnel syndrome experiencing pain is treated with an analgesic system similar to that in Example 2 (3 cm$^2$). The analgesic system is applied to the wrist of the patient. Pain relief is obtained 30 minute following the application and lasted 10-12 hours.

Example 24

Treating Pain Associated with Iliotibial Band Pain

A marathon runner is suffering from iliotibial band pain before a marathon tournament and is expected to have more pain during the running if not treated. An analgesic system similar to that described in Example 3 (180 cm$^2$) is applied to skin area over the pain for one hour and is removed before the running starts. The pain is significantly reduced before the running starts and is much less intense during the running.

It is noted in the above examples that various skin contact area sizes, drug choices, methods of treating specific conditions, etc., are provided for exemplary purposes only. The ranges and choices described in the specification more accurately reflect the appropriate ranges of choices for treating subjects. Thus, while the invention has been described with reference to certain embodiments, those skilled in the art will appreciate that various modifications, changes, omissions, and substitutions can be made without departing from the spirit of the invention. It is therefore intended that the invention be limited only by the scope of the appended claims.

What is claimed is:

1. A method for treating connective tissue pain, comprising:
   a) applying an integrated analgesic system to a skin surface of a subject experiencing connective tissue pain, said analgesic system, comprising:
      i) a heating device configured to heat the skin surface to a temperature of 35° C. to 47° C., and
      ii) a local anesthetic formulation including a eutectic mixture of lidocaine and tetracaine, wherein the local anesthetic formulation is applied to the skin surface over the existing pain;
   b) heating the skin surface to a temperature of 35° C. to 47° C.; and
   c) maintaining the analgesic system on the skin surface for a period of time of at least 2 hours.

2. The method of claim 1, wherein the heating device begins heating at about the same time as the analgesic system is applied to the skin surface.

3. The method of claim 1, wherein the weight percentage of the eutectic mixture is at least 30 wt % of the local anesthetic formulation.

4. The method of claim 1, wherein the local anesthetic formulation has a skin contact region having an area of 2 $cm^2$ to 200 $cm^2$.

5. The method of claim 1, wherein the local anesthetic formulation has a skin contact region having an area of 7 $cm^2$ to 150 $cm^2$.

6. The method of claim 1, wherein the local anesthetic formulation has a skin contact region, said skin contact region having an area of 8 $cm^2$ to 15 $cm^2$.

7. The method of claim 1, wherein the connective tissue pain is ligament pain.

8. The method of claim 1, wherein the connective tissue pain is tendon pain.

9. The method of claim 1, wherein the connective tissue pain is iliotibial band pain.

10. The method of claim 1, wherein the connective tissue pain is associated with a blood vessel.

11. The method of claim 8, wherein the connective tissue pain is caused by tendinopathy.

12. The method of claim 11, wherein the tendinopathy is clavicular or patellar tendonitis.

13. The method of claim 11, wherein the tendinopathy is tennis elbow.

14. The method of claim 11, wherein the tendinopathy is medial tibial stress syndrome.

15. The method of claim 1, wherein the heating device is configured to generate heat by an exothermic oxidative chemical reaction.

16. The method of claim 1, wherein the skin surface is heated to a temperature of 36° C. to 42° C.

17. The method of claim 1, wherein the skin surface is heated to a temperature of 38° C. to 42° C.

18. The method of claim 1, wherein the skin surface is heated to a temperature of 36° C. to 40° C.

19. The method of claim 1, further comprising removing the analgesic system after the period of at least two hours, wherein after removal of the analgesic system, the subject experiences relief of the connective tissue pain for a period of at least 4 hours.

20. The method of claim 1, further comprising removing the analgesic system after the period of at least two hours, wherein after removal of the analgesic system, the subject experiences relief of the connective tissue pain for a period of at least 6 hours.

21. The method of claim 1, further comprising removing the analgesic system after the period of at least two hours, wherein after removal of the analgesic system, the subject experiences relief of the connective tissue pain for a period of at least 12 hours.

* * * * *